United States Patent [19]

Parault

[11] Patent Number: 5,408,889
[45] Date of Patent: Apr. 25, 1995

[54] METHOD AND APPARATUS FOR SAMPLING LIQUIDS FROM VESSELS

[75] Inventor: Leon W. Parault, Port Allen, La.

[73] Assignee: The Dow Chemical Company, Midland, Mich.

[21] Appl. No.: 173,231

[22] Filed: Dec. 27, 1993

[51] Int. Cl.⁶ .............................................. G01N 1/00
[52] U.S. Cl. .............................. 73/863.71; 73/863.81; 73/864.31; 73/864.74; 73/864.34
[58] Field of Search ............ 73/863.71, 863.81–863.83, 73/863.85, 863.86, 864.31, 864.34, 864.65, 864.74

[56] References Cited

U.S. PATENT DOCUMENTS

| | | | |
|---|---|---|---|
| 1,870,436 | 8/1932 | Ball et al. | 73/864.31 |
| 2,006,301 | 6/1935 | Meyer | 73/864.31 |
| 4,986,138 | 1/1991 | Spencer | 73/864.34 |
| 5,265,483 | 11/1993 | Farrell et al. | 73/863.71 |

Primary Examiner—Robert Raevis

[57] ABSTRACT

A hermetic sampling device and method for sampling hazardous fluids that greatly reduces the risk of exposure to operators and the environment. The preferably portable device comprises, a housing having a ball valve at its lower end, the housing adaptable to fit standard valves, such as are commonly found on barges, and a sample catcher movable between the housing and a vessel containing a volume of fluid to be sampled. The sample catcher is lowered from the housing into the vessel to obtain a sample of fluid which is then transferred from the vessel to the housing from where it is further transferred, under pressure, to a hermetically sealed container utilizing hollow needles insertable into the container. When the transfer has been completed, any fluid remaining in the device is returned to the vessel.

6 Claims, 3 Drawing Sheets

METHOD AND APPARATUS FOR SAMPLING LIQUIDS FROM VESSELS

BACKGROUND OF INVENTION

The present invention is concerned with a method and an apparatus for providing improved safety and environmental protection features to the process of sampling fluids from vessels. In many instances it is necessary to obtain fluid samples from storage and transportation vessels such as tanks and barges. Many times this entails working with materials that may be noxious, flammable, or otherwise dangerous to either operators, the environment or both, or release may be regulated by various federal or local rules. The present apparatus is particularly useful as a portable device allowing for easy movement to and from remote sites where samples of materials can be obtained for subsequent analysis.

Conventional sampling methods and devices leave much to be desired, particularly in the area of preventing exposure of operators to certain fluids. Additionally, it is expected that more rigid compliance guidelines will be promulgated by governmental organizations or requested by environmental groups. Also of concern is the necessity of dismantling conventional devices for thorough cleaning to avoid cross contaminating fluids in vessels. These problems are solved by the present invention wherein exposure to potentially harmful fluids are dramatically reduced and any residual sample material is directed back to the sampled vessel so that there is no release to the atmosphere.

SUMMARY OF THE INVENTION

The present invention discloses an apparatus and a method for using the same in the sampling of vessels, such as tanks and barges, with the safety of the operator and the protection of the environment being of the utmost importance. The apparatus is configured to be compatible with standard fittings on tanks and barges thereby reducing the dangers of exposure to hazardous materials when connecting the apparatus to the sampling connection. The apparatus is also designed to be enclosed and to operate under internal pressure such that the collected sample can be transferred to a sample container without any release of the material to the environment, thereby further benefiting the operator and the environment. The portability of the present invention makes it very beneficial for obtaining samples from remote areas, such as barges in the midstream of a river or tied up at remote locations.

The apparatus of the invention can be defined as a sample collection system designed to safely transfer a fluid sample from a vessel containing a fluid to be sampled, such as a barge or tank, to a sample container without substantial release of said fluid to the environment, comprising:

a) a housing having a bottom end and a top end with the bottom end having a sampling point connector sealingly communicating with a sampling point on the vessel and the top end being sealingly closeable;

b) a ball valve situated within the housing adjacent to the sampling point connector;

c) a sample grab means disposed within the housing;

d) means for lowering and raising the sample grab means;

e) means for discharging fluid from the sample grab means into the housing;

f) means for pressurizing the housing;

g) a sample release valve having an inlet end and an outlet with the inlet end connected to the housing and the outlet being connected to a sample container, thereby forming a supply line;

h) a return line connecting the sealable sample container with the housing at a point below the ball valve allowing for the return of fluid to the vessel;

i) a pair of hollow needles mounted proximally to each other so that one of the pair of needles enters the sealable sample container as part of the supply line while the other of the pair of needles exits the sealable sample container as part of the return line.

A process for using the apparatus to safely collect and transfer a fluid sample is also disclosed in the invention. This process includes the steps of:

a) providing a sample collection and transfer apparatus which comprises:
  (i) a housing adapted to sealingly communicate with an hermetic sampling point on the vessel to be sampled;
  (ii) a ball valve located in a lower end of the housing;
  (iii) a sample grab means, having a check valve therein, located within the housing and above the ball valve;
  (iv) means for lowering and raising the sample grab means;
  (v) means for discharging fluid from the sample grab means into the housing;
  (vi) means for pressurizing the housing;
  (vii) a sample release valve which allows fluid to exit the housing;
  (viii) means for conducting the sample fluid from the sample release valve to a sealable sample container;
  (ix) means for sealing the sample container; and
  (x) a pair of hollow needles connecting the conducting means with the sealable sample container, one of the pair of needles piercing the sealing means allowing the sample fluid to enter the sample container, and the other of the pair of needles also piercing the sealing means allowing any gas in the sample container to be conducted back to the vessel via a return line;

b) connecting the sample collection apparatus to the hermetic sampling point on the vessel;

c) opening the ball valve on the sampling device allowing communication therethrough to the vessel;

d) opening the vessel sampling point thereby forming a pathway from the housing to the vessel;

e) lowering the sample grab means through the pathway to a point in the vessel sufficient to catch a fluid sample;

f) raising the sample grab means containing the fluid sample from the vessel to the housing;

g) closing the ball valve;

h) lowering the sample grab means onto the ball of the ball valve so that the checkvalve opens, thereby draining the fluid sample into the housing;

i) connecting the sample container serially with the pair of hollow needles;

j) increasing the pressure inside the housing;

k) opening the sample release valve allowing the fluid sample to flow through the supply line and into the sample container;

l) closing the sample release valve and removing the sample container from the pair of needles;

m) opening the ball valve sufficiently to allow any remaining fluid to return to the vessel without being exposed to the environment;

n) closing the ball valve on the bottom end of the housing;

o) closing the hermetic sampling point; and p) removing the sample collection and transfer apparatus from contact with the hermetic sampling point.

DETAILED DESCRIPTION OF THE PREFERRED EMBODIMENTS

In one embodiment of the invention, the apparatus of the invention is designed to provide an efficient and safe method for sampling vessels such as barges, storage tanks, rail cars, and other such fluid holding units. In a preferred embodiment, the apparatus is designed to be portable so that it may be hand carried to a vessel to be sampled if logistics demand.

Figure 1:
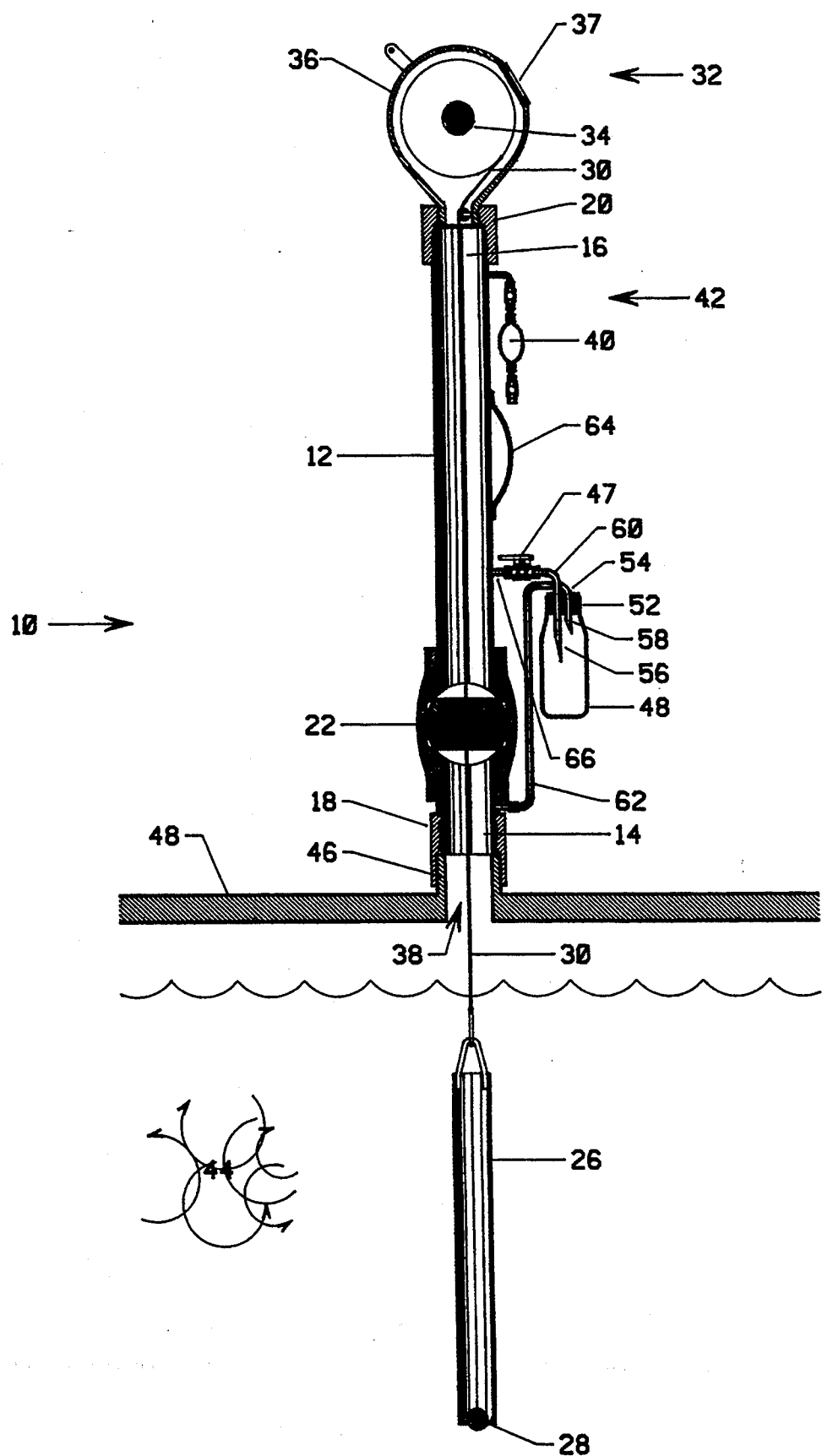
FIG. 1 is a schematic cross sectional view of the sample collecting apparatus of this invention depicting the position of the sample grab means in contact with the fluid in a vessel having passed through the opened ball valve.
Figure 2:
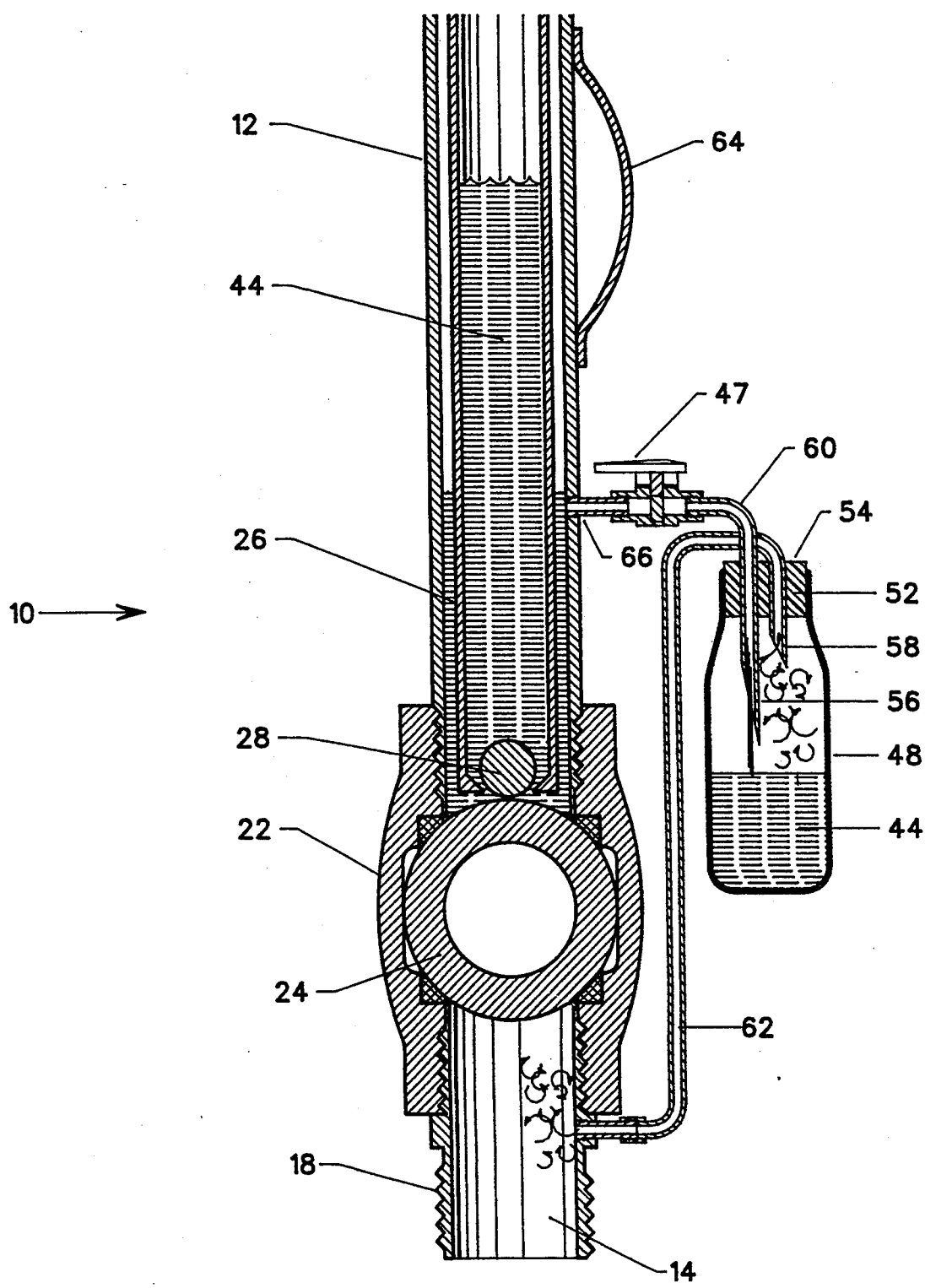
FIG. 2 is a schematic partial cross sectional view depicting the sampled fluid being transferred to a sample container while any gases in the sample container are conducted back through a vent line to the vessel being sampled.
Figure 3:
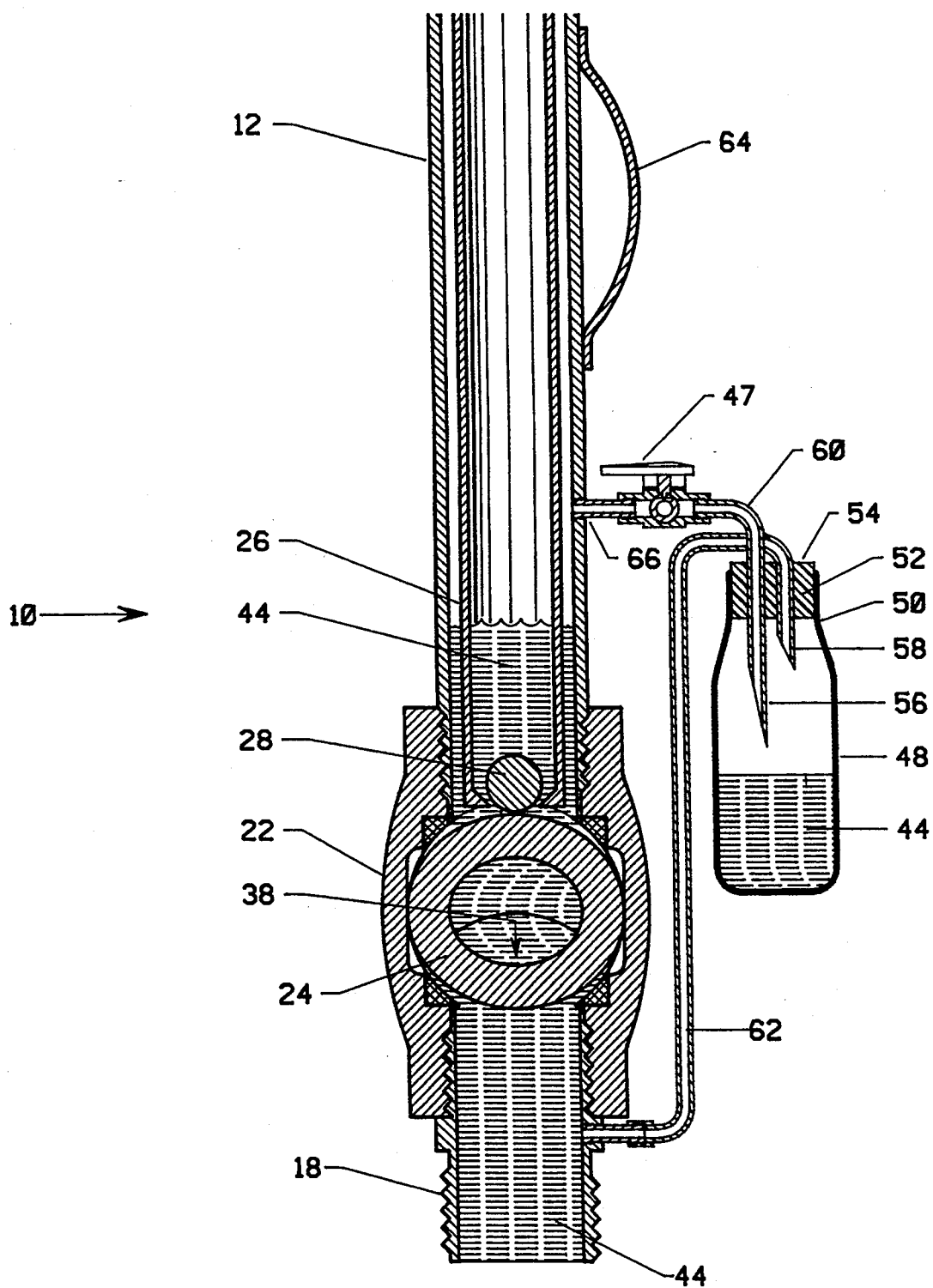
FIG. 3 is a schematic partial cross sectional view depicting the drainage of any residual sampled fluid from the sample catcher or housing back to the vessel.

With particular reference to FIG. 1 of the drawings, reference numeral 10 generally identifies the sample collection system or apparatus of the invention in schematic partial cross sectional form. The apparatus 10 incorporates a housing 12 which is preferably tubular but can be any conventional shape or size sufficient to hold the sample grab means 26 and other components of the system 10. The housing 12 has a hermetic sampling point connector 18 at a bottom end 14 and a means for sealing the housing 12 such as with a pipe cap 20 at a top end 16.

A sample grab means 26, having a ball checkvalve 28 is positioned in the housing 12 and is connected by a wire 30 to a means 32 for raising or lowering the sample grab means 26, which includes a reel device 34 and a crank 36 which can be either manually or electrically operated and optionally a viewing window 37. Adjacent the bottom end 14 of the housing 12 is a ball valve 22 which, in a closed position, prevents communication between the sample grab means 26 and the hermetic sampling point 46 on a vessel 48 to be sampled, such as a barge. Rotation of the ball valve 22 through 180 degrees opens a pathway 38 from the housing 12 to the vessel 48 via the hermetic sampling point 46 such that sample grab means 26 can pass through ball valve 22, through the hermetic sampling point connector 18, and into the vessel 48 containing the fluid 44 to be sampled.

As the sample grab means 26 descends through the fluid 44, it is filled with the fluid 44 to be sampled. Using a reel 34 to raise the sample grab means 26 containing the fluid 44 to be sampled, a checkvalve 28, at the bottom of the sample grab means 26, closes under the weight of the fluid 44 sampled, thereby retaining the fluid 44 to be sampled in the sample grab means 26.

The reeling is continued allowing the sample grab means 26 to pass upwardly through the hermetic sampling point 46, the hermetic valve connector 18 and the ball valve 22, into the housing 12. The ball valve 22 is then returned to its original closed position thereby closing off communication outside of the housing 12. The sample grab means 26 is then lowered to rest on the ball 24 of the ball valve 22 such that the check valve 28 is caused to open allowing the fluid 44 to drain into the housing 12.

The pressure inside the housing 12 is then increased by squeezing the pressure bulb 40 of the pressure applying means 42. Internal pressures in the range of from about 1 psi to about 15 psi have been found to be adequate in the present invention. The sample release valve 47 is then opened. Preferably the sample release valve 47 is adjacent to or a little above the level of the ball valve 22 so that the minimum amount of fluid 44 sample required can be caught.

A sample container 48 having an open end including a sealing means 52, which is preferably a septum 54, is then provided. First and second hollow needles 56 and 58 are then caused to pierce the sealing means 52, extending into the sample container 48. In a preferred embodiment one of the hollow needles 56 is designed to be of sufficient length to enter the container 48, thereby acting as an extension of the supply line 60 while the other hollow needle 58 is designed to be of a shorter length so that it will remain in the headspace of the container 48 and communicate with the vent line 62 which communicates back to the vessel 48 through the housing 12 below the ball valve 22.

Once the needles 56 and 58 are in position, the sample release valve 47 is opened and sample fluid 44 is transported, under pressure, into the sample container 48. When sufficient sample fluid 44 has been collected, the sample release valve 47 is closed and the sample container 48 is removed from needles 56 and 58. The ball valve 22 is then opened sufficiently to allow any remaining fluid 44 from the housing 12 or the sample grab means 26 to drain back into the vessel 48. Ball valve 22 is then closed, the hermetic sampling point 46 is closed, and the sampling apparatus 10 is disconnected from the hermetic sampling point 46.

Thus, a fluid sample has been transported from a vessel, such as a barge, into a closed sample container without allowing any of the contents to escape and endanger the operator or the environment. Any fluid remaining in the housing has been pressured back safely to the vessel.

While the foregoing description is directed to a preferred embodiment of the invention, the scope of the invention is determined by the claims which follow.

What is claimed is:

1. An apparatus for collecting and transferring a sample from a vessel containing a fluid to be sampled to a sealable sample container without substantial release of said fluid to the environment, comprising:

a) a housing having a bottom end and a top end, said bottom end having a sampling point connector adapted to sealingly communicate with a sampling point on said vessel and said top end being sealingly closeable;

b) a ball valve situated within said housing adjacent said sampling point connector adaptor;

c) a sample grab means disposed within said housing;

d) means for lowering and raising said sample grab means;

e) means for discharging said fluid from said sample grab means into said housing;

f) means for pressurizing said housing;

g) a sample release valve having an inlet end and an outlet end, said inlet end connected to said housing with said outlet end connected to a sealable sample container thereby forming a supply line;

h) a return line connecting said sealable sample container with said housing at a point below said ball valve allowing for the return of said fluid to said vessel; and i) a pair of hollow needles mounted proximally to each other such that one of said pair of needles enters said sealable sample container as part of said supply line while the other of said pair of needles exits said sealable sample container as part of said return line.

2. The apparatus of claim 1 wherein said ball valve is a two-way ball valve allowing said sample grab means passage therethrough.

3. The apparatus of claim 2 wherein said sealable sample container is sealed with a septum.

4. The apparatus of claim 3 wherein said raising and lowering means is a hand-operated crank and reel device.

5. The apparatus of claim 4 wherein said pressure is applied by a squeezable bulb.

6. A process for collecting and transferring a sample from a vessel containing a fluid to be sampled to a sample container without substantial release of said fluid to the environment comprising the steps of:

a) providing a sample collection and transfer apparatus which comprises:

(i) a housing adapted to sealingly communicate with an hermetic sampling point on said vessel;

(ii) the ball valve located in a lower end of said housing;

(iii) a sample grab means, having a check valve therein, located within said housing and above said ball valve;

(iv) means for lowering and raising said sample grab means;

(v) means for discharging said fluid from said sample grab means into said housing;

(vi) means for pressurizing said housing;

(vii) a sample release valve which allows fluid to exit said housing;

(viii) means for conducting said sample fluid from said sample release valve to a sealable sample container;

(ix) means for sealing said sample container; and (x) a pair of hollow needles connecting said conducting means with said sealable sample container, one of said pair of needles piercing said sealing means allowing said sample fluid to enter said sample container, and said other of said pair of needles also piercing said sealing means allowing any gas in said sample container to be conducted back to said vessel via a return line;

b) connecting said sample collection apparatus to a sample point on said vessel;

c) opening a ball valve on said sampling device allowing communication therethrough to said vessel;

d) opening said vessel sample point thereby forming a pathway from said housing to said vessel;

e) lowering said sample grab means through said pathway to a point in said vessel sufficient to catch a fluid sample;

f) raising said sample grab means containing said fluid sample from said vessel to said housing;

g) closing said ball valve;

h) lowering said sample grab means onto the ball of said ball valve so that said checkvalve opens, thereby draining said fluid sample into said housing;

i) connecting said sample container serially with said pair of hollow needles;

j) increasing pressure inside of said housing;

k) opening said sample release valve allowing said fluid sample to flow through a supply line into said sample container;

l) closing said sample release valve and removing said sample container from said pair of needles;

m) opening said ball valve sufficiently to allow any remaining fluid to return to said vessel without being exposed to the environment;

n) closing said ball valve on said bottom end of said housing;

o) closing said hermetic sampling point; and p) removing said sample collection and transfer apparatus from contact with said hermetic sampling point.

* * * * *